(12) United States Patent
Nakamura et al.

(10) Patent No.: US 11,981,693 B2
(45) Date of Patent: May 14, 2024

(54) ORGANOGERMANIUM COMPOUND

(71) Applicant: ASAI Germanium Research Institute Co., Ltd., Kawasaki (JP)

(72) Inventors: Takashi Nakamura, Hakodate (JP); Katsuyuki Sato, Hakodate (JP); Yasuhiro Shimada, Hakodate (JP)

(73) Assignee: Asai Germanium Research Institute Co., Ltd., Kanagawa (JP)

( * ) Notice: Subject to any disclaimer, the term of this patent is extended or adjusted under 35 U.S.C. 154(b) by 153 days.

(21) Appl. No.: 17/442,450

(22) PCT Filed: Oct. 26, 2020

(86) PCT No.: PCT/JP2020/040068
§ 371 (c)(1),
(2) Date: Sep. 23, 2021

(87) PCT Pub. No.: WO2021/080019
PCT Pub. Date: Apr. 29, 2021

(65) Prior Publication Data
US 2022/0242890 A1    Aug. 4, 2022

(30) Foreign Application Priority Data

Oct. 24, 2019  (JP) .................................. 2019-193284

(51) Int. Cl.
*C07F 7/30*    (2006.01)

(52) U.S. Cl.
CPC ...................... *C07F 7/30* (2013.01)

(58) Field of Classification Search
CPC ....................................................... C07F 7/30
See application file for complete search history.

(56) References Cited

U.S. PATENT DOCUMENTS

| 4,066,678 | A  | 1/1978 | Sato et al. |
| 5,240,700 | A  | 8/1993 | Sawai et al. |
| 5,744,023 | A  | 4/1998 | Kakimoto et al. |
| 5,783,512 | A  | 7/1998 | Jacobsen et al. |
| 9,546,188 | B2 | 1/2017 | Isaev et al. |
| 9,644,106 | B2 | 5/2017 | Shimanaka et al. |
| 2015/0011523 | A1 | 1/2015 | Isaev et al. |
| 2018/0265527 | A1 | 9/2018 | Moszner et al. |

FOREIGN PATENT DOCUMENTS

| CN | 1131422   | A  | 9/1996 |
| CN | 105143342 | A  | 12/2015 |
| JP | 57102895  | A  | 6/1982 |
| JP | 62252793  | A  | 11/1987 |
| JP | 03206036  | A  | 9/1991 |
| JP | 0466529   | A  | 3/1992 |
| RU | 2476436   | C1 | 2/2013 |

OTHER PUBLICATIONS

Extended European Search Report for European Application No. 20 878 912.3, dated Dec. 2, 2022, 8 pages.
Ambrosov I.V. et al., "Use of Organic Germanium Compounds in Medicine", Drug Development and Registration, 11:144-152, (2015).
Russian Office Action for Russian Application No. 2021133935/04(071709), dated Jun. 30, 2022 with partial translation, 13 pages.
Setkina et al., "Biopharmaceutical Aspects and Bioavailability", Vestnik VGMU, 13(4):162-172 (2014).
International Search Report and Written Opinion for International Application PCT/JP2020/040068, dated Dec. 8, 2020, 5 pages.
Japanese Notice of Reasons for Refusal for Japanese Application No. 2021-500987, dated Mar. 22, 2021, 5 pages.
Mizuno et al., Journal of Pharmaceutical Sciences, 2015, 104:2482-2488.
Nakamura et al., Future Med. Chem., 2015, 7(10), 1233-1246.
Oshita, J., Polymer Preprints, Japan, 2017, vol. 66, No. 2, 1B05, 6 pages.
Shimada et al., Biol. Trace Elem. Res., 2018, 181:164-172.
Tsutsul et al., Journal of the American Chemical Society, 98:25, Dec. 8, 1976, pp. 8287-8289.
Chinese Office Action for Chinese Application No. 202080024839.2, dated Jan. 10, 2024 with translation, 13 pages.

*Primary Examiner* — Alexander R Pagano
*Assistant Examiner* — Frank S. Hou
(74) *Attorney, Agent, or Firm* — Buchanan Ingersoll & Rooney PC

(57) ABSTRACT

The present invention relates to a compound of general formula (I) (wherein R1, R2, and R3 are each independently a hydrogen atom or a lower alkyl and X is an alkali metal cation, ammonium cation, or quaternary ammonium cation). This compound is highly soluble in water, and solutions thereof need not be neutralized when administered to the living body. The compound is useful as a medicine, etc.

4 Claims, 6 Drawing Sheets

ORGANOGERMANIUM COMPOUND

CROSS-REFERENCE TO RELATED APPLICATIONS

This application is a U.S. national phase application of International Application No. PCT/JP2020/040068, filed Oct. 26, 2020, claiming the benefit of Japanese Application No. 2019-193284, filed Oct. 24, 2019, the contents of each of which are incorporated herein by their entireties for all purposes.

FIELD

The present invention relates to an organogermanium compound having a novel structure.

BACKGROUND

Germanium (Ge) is an element that has been studied as a semiconductor for many years, and an organic compound of germanium has been also actively studied, and various types of organogermanium compounds have been synthesized.

For example, Ge-132 (also referred to as poly-trans-[(2-carboxyethyl)germasesquioxane], Repagermanium, or Asaigermanium) is an organogermanium compound having various physiological effects, such as immunostimulatory effects, anti-tumor effects, anti-inflammatory effects, analgesic effects, and co-operative effects with morphine. Ge-132 is a crystalline compound being in a solid form at room temperature and having a cyclic structure composed of a total of 12 germanium and oxygen atoms, and is hydrolyzed in water to a monomer, namely, 3-(trihydroxygermyl) propanoic acid (THGP). Since a living body is rich in water, Ge-132 is thought to undergo hydrolysis in the living body to generate THGP or its salt.

THGP is thought to form a lactone-type THGP-cis-diol complex through dehydration condensation with a cis-diol-containing compound, and thereby to regulate physiological functions of the cis-diol-containing compound (for example, Non Patent Literature 1). As an example of the regulation of physiological functions by their interaction, it has been reported that THGP forms a complex with adenosine or ATP to inhibit adenosine or ATP from binding to a P1 or P2 receptor and thus can be involved in pain suppression (Non Patent Literature 2). These findings suggest that Ge-132 exerts its various physiological effects through the interaction of THGP, which is produced by hydrolysis in a living body, with components contained in the body.

Drying a solution of THGP produces solid organogermanium compounds having a polymer structure in which a plurality of THGPs are dehydrated and condensed. Ge-132 is one of solid organogermanium compounds produced in this way, and there are other known solid organogermanium compounds such as poly-[(2-carboxyethyl-hydroxygermanium)oxide], a solid organogermanium compound having a linear-polymer structure, and propagermanium(3-oxygermylpropionic acid polymer), a solid organogermanium compound having a ladder structure (a cyclic structure composed of a total of 8 germanium and oxygen atoms) (Patent Literature 1, Non Patent Literatures 3 and 4). These solid organogermanium compounds are presumed to undergo hydrolysis in a solvent containing water to produce THGP, which in turn exhibits the various physiological effects described above. Therefore, it is favorable for solid organogermanium compounds expected to exhibit the physiological effects to be those that are more easily to produce THGP, i.e., those that are excellent in solubility, specifically, those that have high solubility and a high dissolution rate.

However, conventional solid organogermanium compounds are insufficiently soluble in water, and it takes time to hydrolyze and dissolve conventional solid organogermanium compounds in water, in other words, conventional solid organogermanium compounds have a lower dissolution rate. In addition, a solution of conventional solid organogermanium compounds has an acidic pH, and accordingly, when the solution is administered to a living body, neutralization of the solution may be necessary.

CITATION LIST

Patent Literature

Patent Literature 1: Japanese Patent Application Laid-open Publication No. 57-102895

Non-Patent Literature

Non-Patent Literature 1: Nakamura et al., Future. Med. Chem., 2015, 7 (10), 1233-1246.

Non-Patent Literature 2: Shimada et al., Biol. Trace Elem. Res., 2018, 181 (1), 164-172.

Non-Patent Literature 3: Tsutsui et al., J. Am. Chem. Soc., 1976, 98 (25), 8287-8289.

Non-Patent Literature 4: Mizuno et al., J. Pharm. Sci., 2015, 104 (8), 2482-2488.

SUMMARY

Technical Problem

An object of the present invention is to provide a novel organogermanium compound excellent in solubility.

Solution to Problem

The present inventors made an intensive study on the crystallization of THGP. As a result, the present inventors have found that a uniform single crystal was produced by neutralizing an aqueous solution containing a high concentration of THGP with alkali and adding an organic solvent miscible with water, such as alcohol, and that this crystal was a cage-type octamer in which 8 THGP molecules were associated, and completed the following invention.

(1) A compound of formula (I),

[Chemical Formula 1]

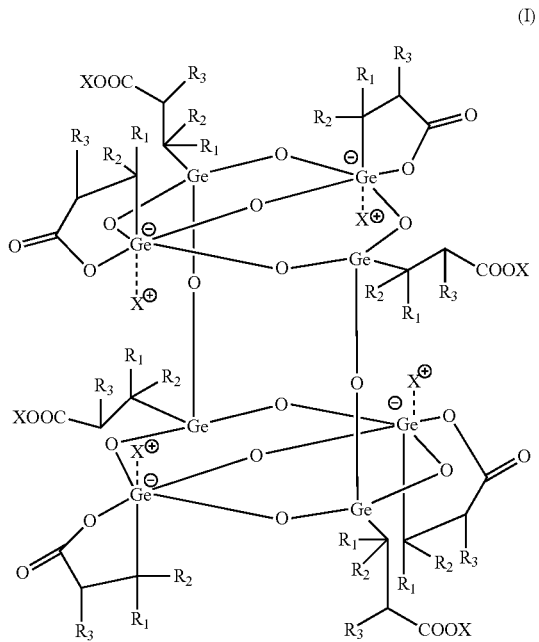

wherein $R_1$, $R_2$, and $R_3$ are each independently hydrogen or lower alkyl, and X is an alkali metal cation, an ammonium cation, or a quaternary ammonium cation.

(2) The compound according to (1), wherein all of $R_1$, $R_2$, and $R_3$ are hydrogen.

(3) The compound according to (1), wherein X is a sodium cation.

(4) The compound according to (1), wherein all of $R_1$, $R_2$, and $R_3$ are hydrogen, and X is a sodium cation.

Advantageous Effects of Invention

According to the present invention, it is possible to provide an organogermanium compound that is excellent in solubility and does not require a neutralization process when administered to a living body.

DESCRIPTION OF EMBODIMENTS

Figure 1:
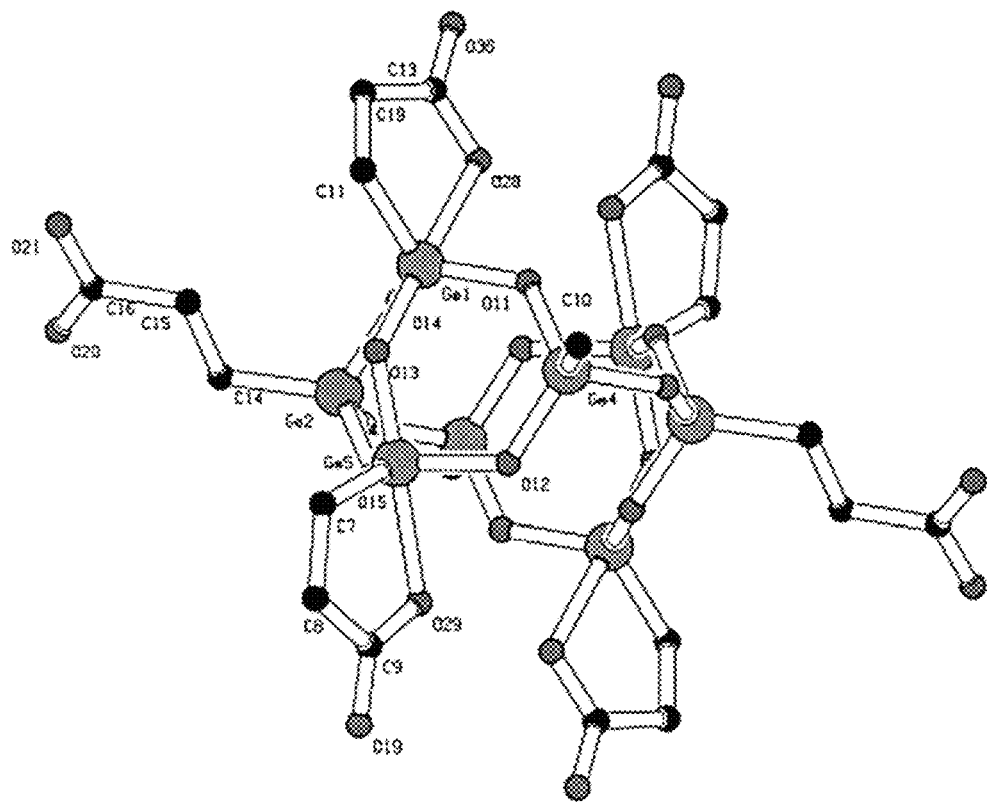
FIG. 1 is a diagram of the structural model of a THGP octamer as an example of a compound according to the present invention.

While the following descriptions of the present invention may be based on representative embodiments or specific examples, the present invention is not limited to such embodiments or examples. Note that, in the present specification, the upper limits and the lower limits of numerical ranges can be arbitrarily combined. Furthermore, in the present specification, a numerical range expressed using "to" or "-" means a range including numerical values at both ends of the range as an upper limit and a lower limit, unless otherwise specified.

A first aspect of the present invention relates to a compound of formula (I),

[Chemical Formula 2]

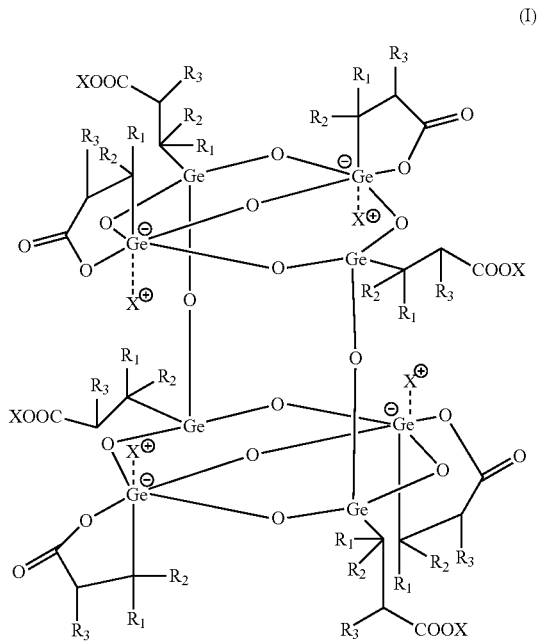

wherein $R_1$, $R_2$, and $R_3$ are each independently hydrogen or lower alkyl, and X is an alkali metal cation, an ammonium cation, or a quaternary ammonium cation.

$R_1$, $R_2$, and $R_3$ in formula (I) are each independently hydrogen or lower alkyl. The lower alkyl refers to a linear or branched alkyl having 1 to 6, preferably 1 to 4, and more preferably 1 to 3 carbon atoms. In a preferred embodiment, all of $R_1$, $R_2$, and $R_3$ are hydrogen.

X in formula (I) is an alkali metal cation such as $Na^+$ or $K^+$, an ammonium cation, or a quaternary ammonium cation. The quaternary ammonium cation is a cation in which four alkyl groups and/or aryl groups are bonded to nitrogen. The quaternary ammonium cation preferably used in the present invention is a cation in which four linear or branched alkyl groups having 1 to 6, preferably 1 to 4, and more preferably 1 to 3 carbon atoms are bonded to nitrogen. Examples of the quaternary ammonium cation include a tetramethyl ammonium cation, a tetraethyl ammonium cation, a tetrapropyl ammonium cation, ethyltrimethyl ammonium, and triethylmethyl ammonium. In a preferred embodiment, X is $Na^+$.

The compound of formula (I) can be also expressed by formula (II). $R_1$, $R_2$, $R_3$, and X in formula (II) are the same as those defined in formula (I).

[Chemical Formula 3]

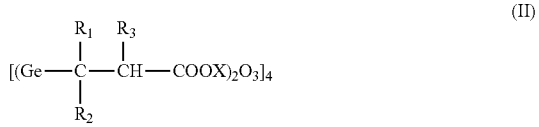

(II)

Preferred examples of the compound of formula (I) can include the compound of formula (I) in which all of $R_1$ to $R_3$ are hydrogen and X is Nat, that is, 1, 7, 9, 15-tetra(2'-sodium carboxyethylgermanium)-3, 5, 11, 13-tetra-[sodium propanato(2-)-$C^{3'}$, $O'$]-germanium-2, 4, 6, 8, 10, 12, 14, 16, 17, 18, 19, 20-dodecaoxa-pentacyclo[$8.1^{1,5}.1^{7,11}.1^{9,13}.1^{3,15}$.] icosane (hereinafter, referred to as a THGP octamer).

The compound of formula (I) can be produced by crystallizing a compound of formula (III) (in which $R_1$ to $R_3$ are the same as those described in the description of formula (I)) in a mixed solvent of water and an organic solvent miscible with water.

[Chemical Formula 4]

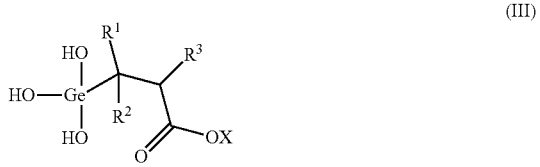

(III)

The compound of formula (III) can be synthesized using an acrylic acid derivative of formula (IV) and trichlorogermane, as illustrated in the following scheme.

[Chemical Formula 5]

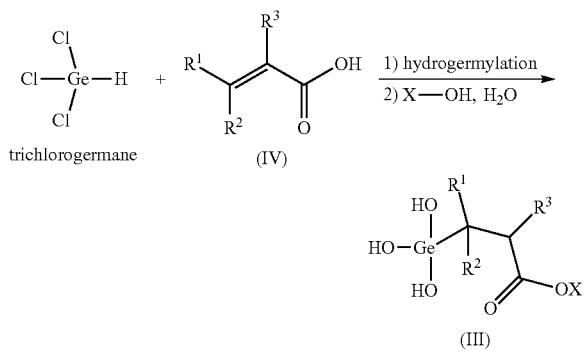

The hydrogermylation of the acrylic acid derivative of formula (IV) and trichlorogermane can be performed, for example, using concentrated hydrochloric acid, diethyl ether, or chloroform as a solvent, at a temperature of approximately 25° C. to 40° C. The compound resulting from the hydrogermylation is then reacted with an alkali metal hydroxide or amine in the presence of water, typically in an aqueous solution, to undergo hydrolysis and neutralization, whereby the compound of formula (III) can be prepared.

Alternatively, a known THGP polymer, such as Ge-132, is reacted with an alkali metal hydroxide or amine in the presence of water, whereby the compound of formula (III) in which $R_1$ to $R_3$ are hydrogen can be prepared.

The obtained compound of formula (III) is crystallized in a mixed solvent of water and an organic solvent miscible with water. A mixing ratio of water to the organic solvent in the mixed solvent can be 1:3 to 1:20 (v/v), preferably 1:3 to 1:10 (v/v), and more preferably 1:3 to 1:5 (v/v). Examples of the organic solvent to be used include acetone or lower alcohol, such as methanol, ethanol, 1-propanol, or 2-propanol, and ethanol is more preferably used.

To an aqueous solution of the compound of formula (III), the above organic solvent in an amount that brings the mixing ratio into the above range is added, whereby a mixed solution for crystallization is prepared. The concentration of the compound of formula (III) in the mixed solution can be 2% to 12% (w/v), for example, 4% to 12% (w/v), 6% to 12% (w/v), or 8% to 12% (w/v), and is preferably 8% to 12% (w/v).

The above mixed solution is sufficiently stirred, and then left standing at room temperature for 12 hours or longer, preferably 24 hours or longer, whereby a crystal of the compound of formula (I) can be precipitated. In order to promote the crystallization, a crystal of the compound of formula (I) may be added as a seed crystal. The obtained crystal can be isolated from the mixed solution and purified by a known method, such as filtration, washing with an organic solvent, such as a lower alcohol, and drying under reduced pressure.

Thus, the present invention also provides a method for producing the compound of formula (I), the method including mixing a solution in which the compound of formula (III) is dissolved and a mixed solvent in which water and an organic solvent miscible with water are mixed at a ratio of 1:3 to 1:20 (v/v) so as to achieve a concentration of the compound of formula (III) of 2% to 12% (w/v); and leaving the resulting mixed solution standing to precipitate a crystal of the compound of formula (I).

The compound of formula (I) can be produced as a crystal by the production method described above, and the crystal is another aspect of the present invention. The crystal of the THGP octamer has a size of 8 μm×2 μm and is plate-like in shape. Furthermore, by evaporating the organic solvent from a saturated solution of this crystal in an organic solvent, the crystal can be recrystallized. A single crystal of the THGP octamer recrystallized by using methanol as an organic solvent shows the following crystal data when subjected to X-ray diffraction measurement.

Crystal system: triclinic
Space group: P-1
Lattice constant: a=11.8879(7), b=20.6589(12), c=22.5198(13), α=63.5610(10), β=76.4800(10), γ=81.3480(10)
Unit lattice volume: V=4808.14

In X-ray diffraction measurements, a measurement error may occur depending on measurement conditions. Therefore, the crystal of the compound of formula (I) is not limited to a crystal that gives crystal data identical to the crystal data described above, and a crystal that gives crystal data substantially identical to the crystal data described above is also within the scope of the present invention. By suitably changing measurement conditions, those skilled in the art can confirm that crystal data are substantially identical.

Not all of the crystals of the compound of formula (I) give the above crystal data. Those skilled in the art will understand that a crystal giving the above crystal data is only one form of the crystals of the compound of formula (I), and that there can be other forms of the crystals of the compound of formula (I).

The compound of formula (I) are extremely soluble in water and dissolve quickly. For example, the solubility (the mass (g) of a solute in 100 g of a saturated solution) of Ge-132 in water having 20° C. is approximately 1% (in other words, the mass of Ge-132 in 100 g of the saturated solution having 20° C. is approximately 1 g), and the time required for complete dissolution of 1% Ge-132 in water at the same temperature is 30 minutes or longer. Under the same conditions, the solubility of the THGP octamer is 58.8%, and the dissolving time of the THGP octamer is approximately 10 seconds. The pH of the aqueous solution in which the THGP octamer is dissolved is neutral, similar to the pH of a living body. Furthermore, the compound of formula (I) is soluble in some organic solvents, such as methanol, in which the existing THGP polymers are insoluble.

The compound of formula (I) is hydrolyzed in water to produce a water-soluble organogermanium compound, which is the constituent unit of the compound of formula (I). Such water-soluble organogermanium compound is capable of interacting with a compound having a cis-diol structure (such as adenosine or fructose) or a compound having a thiol structure (such as $H_2S$ or glutathione) in an aqueous solution. The water-soluble organogermanium compound is also capable of suppressing pain and mechanical allodynia caused by a substance that can interact with the water-soluble organogermanium compound. Furthermore, the water-soluble organogermanium compound is capable of protecting a functional group of a substance that can interact with the water-soluble organogermanium compound, or is capable of reducing the volatility of the substance, when dissolved in water together with the substance. Therefore, the compound of formula (I) can be used for similar applications as Ge-132, such as suppression of pain and mechanical allodynia, protection of a cis-diol group-containing compound, protection of a thiol group-containing compound, suppression of pain or itching caused by hydrogen sulfide, deodorization or odor prevention, and suppression of the production of type I interferon.

For a living body, the compound of formula (I) can be used in the form of a pharmaceutical composition, a food composition, or a cosmetic composition, each further contains pharmaceutically acceptable ingredients including a buffer, a stabilizer, a preservative, and an excipient, or the like, and/or other active ingredients. These compositions are another aspect of the present invention. The pharmaceutically acceptable ingredients are well known to those skilled in the art, and can be appropriately selected and used by those skilled in the art, within the scope of their ordinary implementation ability, for example, from ingredients described in the Japanese Pharmacopoeia, 17th Edition or other written standards, depending on the form of a preparation.

The pharmaceutical composition containing the compound of formula (I) can be used for the treatment of a disease or the alleviation of a symptom to which organogermanium compounds, in particular, THGPs are effective, for example, the treatment of cancer or infectious diseases or the alleviation of inflammation or pain. Thus, the present invention provides a method for treating a disease or alleviating a symptom to which organogermanium compounds, in particular, THGPs are effective, the method including administering an effective dose of a pharmaceutical composition containing the compound of formula (I) to a subject. Examples of the disease include tumors and infectious diseases. Examples of the symptom include inflammation and pain.

In the present invention, the pharmaceutical composition described above can be in any form, and preferred examples of the form include oral preparations (such as tablets, capsules, powders, granules, fine granules, pills, suspensions, emulsions, liquids, and syrups) and topical preparations (such as ointments and adhesive patches).

The method for administering the pharmaceutical composition is not particularly limited, and is suitably determined depending on its dosage form. In one preferred embodiment, the composition is orally or percutaneously administered to a living body.

The dose of the composition is suitably selected, depending on the usage, the age of the subject, the type and site of the disease, and other conditions, and is generally 10 µg to 2000 µg, preferably 50 µg to 1000 µg, and more preferably 100 µg to 500 µg per kilogram of body weight of an adult. The dose of the pharmaceutical composition can be administered once a day, or divided into multiple doses in a day, or can be administered intermittently.

The present invention will be described in more detail by the following examples, without being limited to the examples.

EXAMPLES

Example 1 Synthesis and Structure Analysis of THGP Octamer

1) Synthesis

Ge-132 (500 g, 2.95 mol in terms of monomer) was weighed in a 2 L beaker, and added 1 L of distilled water, then suspended. 95% sodium hydroxide (124 g, 2.95 mol) was weighed in a Teflon (registered trademark) container, and added 500 mL of distilled water, then dissolved. Aqueous sodium hydroxide solution was added to the Ge-132 water suspension in several portions with stirring to neutralize and dissolve Ge-132. The neutralized solution was transferred to a 2-L eggplant flask and heated under reduced pressure, and concentrated to approximately 1 L. The concentrated solution was transferred to a 5-L container, 3 L of ethanol was added, and the mixture was stirred thoroughly and allowed to stand for 24 hours at room temperature. The precipitated crystals were collected by suction filtration, air-dried, and then heated in a glass tube oven at 105° C. for 8 hours or longer under reduced pressure to dryness, to obtain the target compound as white crystals in 95% yield. The obtained crystals had a size of 8 µm×2 µm and was plate-like in shape.

2) Single Crystal X-Ray Structure Analysis

The crystals obtained in 1) were dissolved in methanol to prepare a saturated methanol solution. The saturated methanol solution was left to stand at room temperature without tightly sealing, and the methanol was gradually evaporated to obtain plate-like crystals that grew to 1 mm or more. The crystals were collected and the X-ray diffraction intensities were measured using a single crystal X-ray structure analyzer (SMART APEX II ULTRA, Bruker) under the following conditions.

Detector: Bruker APEXII CCD area detector
Light source type: Bruker TXS fine-focus rotating anode
Wavelength used: Mo 0.71073 Å
Tube current: 24 mA
Tube voltage: 50 kv
Scan width: 0.5°

Exposure time: 3 sec
Analysis software and method:
data_collection 'APEX2'
cell_refinement 'APEX2 (Bruker AXS, 2006)'
data_reduction 'SAINT (Bruker AXS, 2004)'
structure_solution 'SHELXS-97 (Sheldrick, 1997)'
structure_refinement 'SHELXL-97 (Sheldrick, 1997)'
molecular_graphics 'XSHEL (Bruker AXS, 2002)'
publication_material 'XCIF (Bruker AXS, 2001)'

The parameters of the determined crystal structure are shown below, the atomic coordinates are shown in Table 1, and the molecular structure constructed from them is illustrated in FIG. 1.

Crystal system: triclinic
Space group: P −1
Lattice constant: a=11.8879(7), b=20.6589(12), c=22.5198(13), α=63.5610(10), β=76.4800(10), γ=81.3480(10)
Unit lattice volume: V=4808.14

TABLE 1

| Number | Label | Charge | SybylType | Xfrac + ESD | Yfrac + ESD | Zfrac + ESD | Symm. op. |
|---|---|---|---|---|---|---|---|
| 1 | C1B | 0 | C.3 | 0.514(2) | 0.9335(11) | 0.7436(8) | x, y, z |
| 2 | C2B | 0 | C.3 | 0.456(2) | 0.9901(13) | 0.7671(12) | x, y, z |
| 3 | C3B | 0 | C.2 | 0.3845(17) | 1.0449(9) | 0.7188(9) | x, y, z |
| 4 | C4B | 0 | C.3 | 0.7894(16) | 0.7949(11) | 0.5957(10) | x, y, z |
| 5 | C5B | 0 | C.3 | 0.8761(18) | 0.7845(15) | 0.5400(10) | x, y, z |
| 6 | C6B | 0 | C.2 | 0.8296(13) | 0.8152(11) | 0.4759(8) | x, y, z |
| 7 | C7B | 0 | C.3 | 0.828(3) | 1.0476(18) | 0.5492(18) | x, y, z |
| 8 | C8B | 0 | C.3 | 0.899(2) | 0.9693(17) | 0.5946(17) | x, y, z |
| 9 | C9B | 0 | C.2 | 1.0109(17) | 0.9895(8) | 0.6078(11) | x, y, z |
| 10 | C10B | 0 | C.3 | 0.388(3) | 0.769(2) | 0.6735(17) | x, y, z |
| 11 | C11B | 0 | C.3 | 0.276(3) | 0.7622(19) | 0.7385(16) | x, y, z |
| 12 | C12B | 0 | C.2 | 0.2797(19) | 0.6891(16) | 0.804(2) | x, y, z |
| 13 | Ge1B | 0 | Ge | 0.5132(2) | 0.95463(13) | 0.65075(12) | x, y, z |
| 14 | Ge2B | 0 | Ge | 0.7018(2) | 1.03765(13) | 0.52384(12) | x, y, z |
| 15 | Ge3B | 0 | Ge | 0.6757(2) | 0.87376(13) | 0.56283(12) | x, y, z |
| 16 | Ge4B | 0 | Ge | 0.4077(2) | 0.85926(13) | 0.60473(12) | x, y, z |
| 17 | O1B | 0 | O.3 | 0.3943(10) | 0.9300(9) | 0.6292(8) | x, y, z |
| 18 | O2B | 0 | O.3 | 0.5682(8) | 1.0336(9) | 0.5830(6) | x, y, z |
| 19 | O3B | 0 | O.3 | 0.7126(14) | 0.9649(4) | 0.5040(7) | x, y, z |
| 20 | O4B | 0 | O.3 | 0.5439(8) | 0.8576(10) | 0.5494(7) | x, y, z |
| 21 | O5B | 0 | O.3 | 0.6207(12) | 0.8882(8) | 0.6379(6) | x, y, z |
| 22 | O6B | 0 | O.co2 | 0.3193(13) | 1.0906(8) | 0.7371(8) | x, y, z |
| 23 | O7B | 0 | O.co2 | 0.3793(12) | 1.0382(8) | 0.6655(8) | x, y, z |
| 24 | O8B | 0 | O.co2 | 0.8879(13) | 0.8030(9) | 0.4261(7) | x, y, z |
| 25 | O9B | 0 | O.co2 | 0.7353(12) | 0.8551(9) | 0.4690(6) | x, y, z |
| 26 | O10B | 0 | O.3 | 0.3101(14) | 0.8813(9) | 0.5485(8) | x, y, z |
| 27 | O11B | 0 | O.co2 | 1.0372(15) | 1.0524(9) | 0.5866(9) | x, y, z |
| 28 | O12B | 0 | O.co2 | 1.0675(19) | 0.9348(11) | 0.6398(11) | x, y, z |
| 29 | O13B | 0 | O.co2 | 0.181(2) | 0.6671(16) | 0.8219(15) | x, y, z |
| 30 | O14B | 0 | O.co2 | 0.369(3) | 0.6492(18) | 0.8075(19) | x, y, z |
| 31 | C1B | 0 | C.3 | 0.486(2) | 1.0665(11) | 0.2564(8) | 1-x, 2-y, 1-z |
| 32 | C2B | 0 | C.3 | 0.544(2) | 1.0099(13) | 0.2329(12) | 1-x, 2-y, 1-z |
| 33 | C3B | 0 | C.2 | 0.6155(17) | 0.9551(9) | 0.2812(9) | 1-x, 2-y, 1-z |
| 34 | C4B | 0 | C.3 | 0.2106(16) | 1.2051(11) | 0.4043(10) | 1-x, 2-y, 1-z |
| 35 | C5B | 0 | C.3 | 0.1239(18) | 1.2155(15) | 0.4600(10) | 1-x, 2-y, 1-z |
| 36 | C6B | 0 | C.2 | 0.1704(13) | 1.1848(11) | 0.5241(8) | 1-x, 2-y, 1-z |
| 37 | C7B | 0 | C.3 | 0.172(3) | 0.9524(18) | 0.4508(18) | 1-x, 2-y, 1-z |
| 38 | C8B | 0 | C.3 | 0.101(2) | 1.0307(17) | 0.4054(17) | 1-x, 2-y, 1-z |
| 39 | C9B | 0 | C.2 | −0.0109(17) | 1.0105(8) | 0.3922(11) | 1-x, 2-y, 1-z |
| 40 | C10B | 0 | C.3 | 0.612(3) | 1.231(2) | 0.3265(17) | 1-x, 2-y, 1-z |
| 41 | C11B | 0 | C.3 | 0.724(3) | 1.2378(19) | 0.2615(16) | 1-x, 2-y, 1-z |
| 42 | C12B | 0 | C.2 | 0.7203(19) | 1.3109(16) | 0.196(2) | 1-x, 2-y, 1-z |
| 43 | Ge1B | 0 | Ge | 0.4868(2) | 1.04537(13) | 0.34925(12) | 1-x, 2-y, 1-z |
| 44 | Ge2B | 0 | Ge | 0.2982(2) | 0.96235(13) | 0.47616(12) | 1-x, 2-y, 1-z |
| 45 | Ge3B | 0 | Ge | 0.3243(2) | 1.12624(13) | 0.43717(12) | 1-x, 2-y, 1-z |
| 46 | Ge4B | 0 | Ge | 0.5923(2) | 1.14074(13) | 0.39527(12) | 1-x, 2-y, 1-z |
| 47 | O1B | 0 | O.3 | 0.6057(10) | 1.0700(9) | 0.3708(8) | 1-x, 2-y, 1-z |
| 48 | O2B | 0 | O.3 | 0.4318(8) | 0.9664(9) | 0.4170(6) | 1-x, 2-y, 1-z |
| 49 | O3B | 0 | O.3 | 0.2874(14) | 1.0351(4) | 0.4960(7) | 1-x, 2-y, 1-z |
| 50 | O4B | 0 | O.3 | 0.4561(8) | 1.1424(10) | 0.4506(7) | 1-x, 2-y, 1-z |
| 51 | O5B | 0 | O.3 | 0.3793(12) | 1.1118(8) | 0.3621(6) | 1-x, 2-y, 1-z |
| 52 | O6B | 0 | O.co2 | 0.6807(13) | 0.9094(8) | 0.2629(8) | 1-x, 2-y, 1-z |
| 53 | O7B | 0 | O.co2 | 0.6207(12) | 0.9618(8) | 0.3345(8) | 1-x, 2-y, 1-z |
| 54 | O8B | 0 | O.co2 | 0.1121(13) | 1.1970(9) | 0.5739(7) | 1-x, 2-y, 1-z |
| 55 | O9B | 0 | O.co2 | 0.2647(12) | 1.1449(9) | 0.5310(6) | 1-x, 2-y, 1-z |
| 56 | O10B | 0 | O.3 | 0.6899(14) | 1.1187(9) | 0.4515(8) | 1-x, 2-y, 1-z |
| 57 | O11B | 0 | O.co2 | −0.0372(15) | 0.9476(9) | 0.4134(9) | 1-x, 2-y, 1-z |
| 58 | O12B | 0 | O.co2 | −0.0675(19) | 1.0652(11) | 0.3602(11) | 1-x, 2-y, 1-z |
| 59 | O13B | 0 | O.co2 | 0.819(2) | 1.3329(16) | 0.1781(15) | 1-x, 2-y, 1-z |
| 60 | O14B | 0 | O.co2 | 0.631(3) | 1.3508(18) | 0.1925(19) | 1-x, 2-y, 1-z |

It was confirmed that the crystals obtained in 1) were organogermanium compounds having a structure in which eight THGPs was dehydrated and condensed ((1,7,9,15-tetra(2'-sodium carboxyethylgermanium)-3,5,11,13-tetra-[sodium propanato(2-)-$C^{3'},O'$]-germanium-2,4,6,8,10,12,14,16, 17,18,19,20-dodecaoxa-pentacyclo[$8.1^{1,5}.1^{7,11}.1^{9,13}.1^{3,15}$.] icosane), THGP octamer) (See FIG. 1 and Table 1). The characteristic features of the octamer are that four of the propion chains in the eight THGPs constituting the octamer have a linear structure while the remaining four propion chains have a lactone structure, and that the germanium atoms in the lactone structure are five-coordinated.

3) Solubility

To 100 mg of the THGP octamer obtained in (1), the process of adding purified water or methanol in small portions and stirring for 30 minutes at room temperature was repeated, and the volume of the solution was measured when the THGP octamer was visually observed to as completely dissolved. The solubility of the THGP octamer (Solute Amount (g)/Total Mass (g)×100%) was calculated from the measured volume. Furthermore, the pH of the solution was measured when the THGP octamer was completely dissolved.

Conventional THGP polymers, including Ge-132, have solubility of approximately 1% in water, and are insoluble in organic solvents, such as methanol. In contrast, the solubility of the THGP octamer was 58.8% in water and 1.4% in methanol, respectively. Moreover, the pH of the aqueous solution was around 7.5, which is near neutral.

4) Dissolution Rate 100 mg of Ge-132 and 100 mg of the THGP octamer were added to 10 mL of purified water, respectively, and the mixtures were stirred at 300 rpm at room temperature, and then the time required to be visually observed as completely dissolved was measured.

When conventional THGP polymers, including Ge-132, are dissolved in water at room temperature, it takes some time for the crystals to dissolve completely. The time required for the crystals to completely dissolve during the preparation of Ge-132 1% aqueous solution was measured, and it was confirmed that 30 minutes or more was required. In contrast, the THGP octamer was completely dissolved in approximately 10 seconds.

5) Laser Diffraction Particle Size Distribution

The particle size distribution of the THGP octamer was measured using a laser diffraction particle size analyzer (HRA, Microtrac) with ethanol as the dispersant after 1 minute of ultrasonic dispersion. The measurement conditions were as follows.

Figure 2:
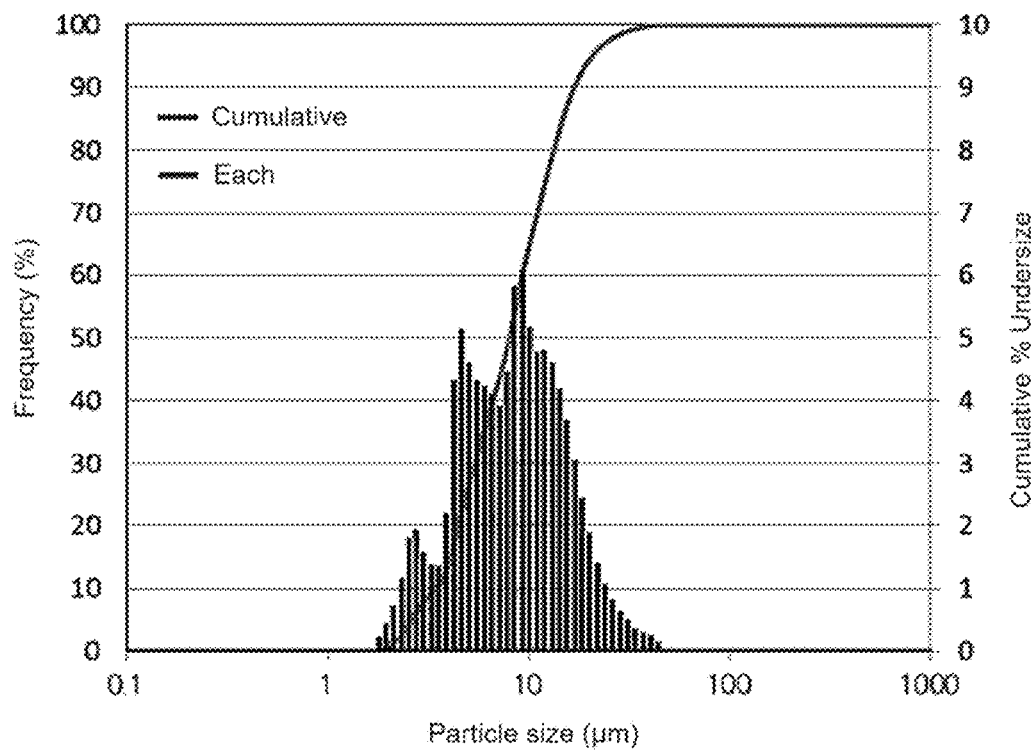
FIG. 2 is a diagram of the particle size distribution of the THGP octamer.

Measurement range: 0.06 μm to 1400 μm
Light source used: carbon dioxide laser×3
Detector: scattered light detector The THGP octamer was confirmed to be very fine particles, with Dp10=3.4 μm, Dp50 (median diameter)=8.0 μm, and Dp90=16.9 μm (see FIG. 2).

6) Infrared Spectrophotometric Analysis

The mixture of potassium bromide (KBr) and the THGP octamer and the mixture of KBr and Ge-132, each in pellet form, were subjected to infrared spectroscopic analysis using an infrared spectrophotometer (FTIR-8100M, Shimadzu Corporation). The analysis conditions were as follows.

Figure 3:
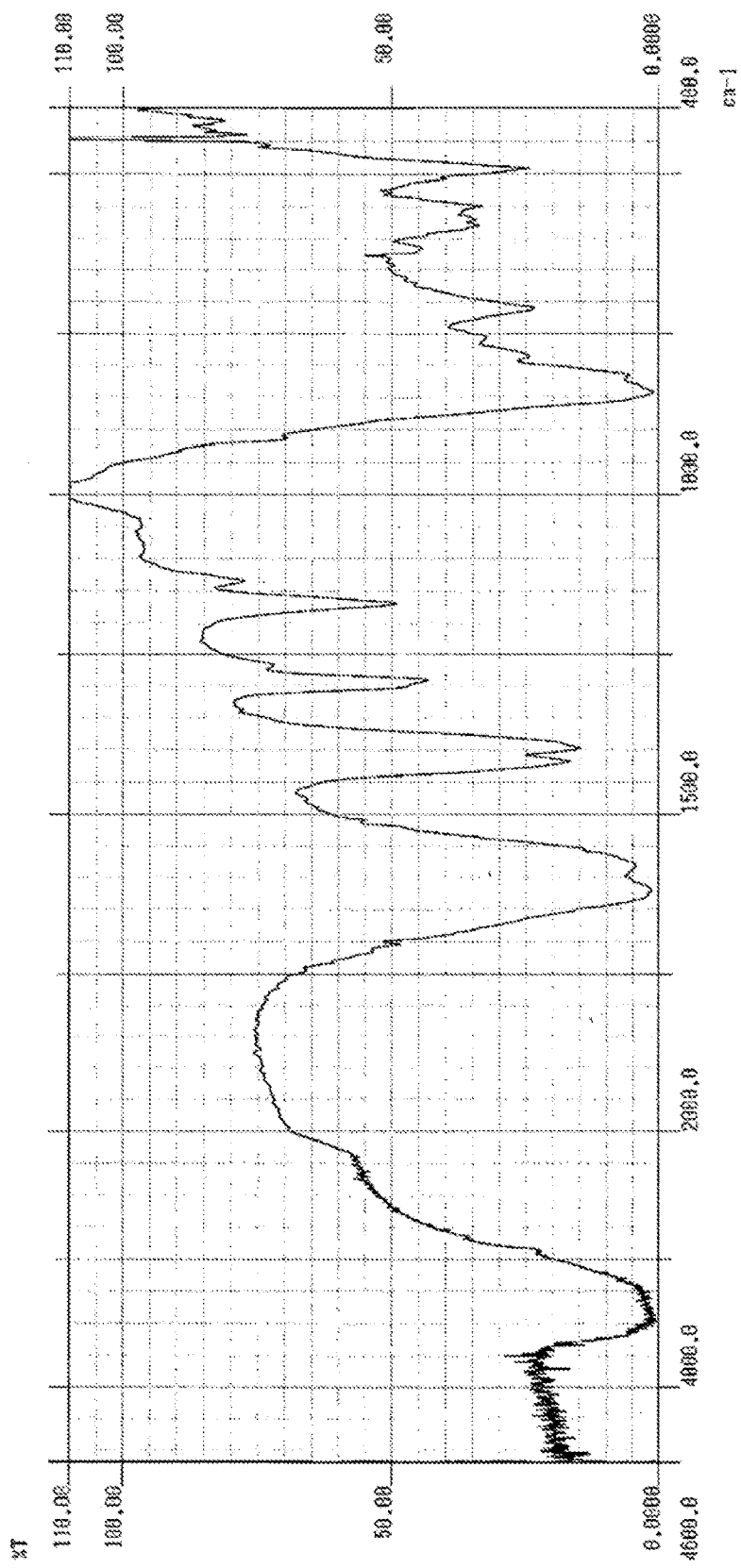
FIG. 3 is a diagram of the infrared absorption spectrum of the THGP octamer.

Measurement method: KBr pellet method
Measurement range: 400 $cm^{-1}$ to 4600 $cm^{-1}$
Resolution: 4 $cm^{-1}$
Mirror speed: 2.8 mm/sec
Number of scans: 40 times It was confirmed that the absorption due to C=O at 1700 $cm^{-1}$ in Ge-132 shifted to lower wavenumber from 1650 to 1550 $cm^{-1}$ in the THGP octamer, that the absorption due to carboxylic acid at 3000 $cm^{-1}$ in Ge-132 disappeared in the THGP octamer, and that the spectrum of Ge-132 and the spectrum of the THGP octamer were different to each other in a fingerprint region of 1500 $cm^{-1}$ or less (see FIG. 3).

7) Mass Spectroscopy

A methanol solution of the THGP octamer was subjected to mass spectrometry (TOF-MS, QToF Ultima, Waters) for mass analysis. The analysis conditions were as follows.

Ionization mode: ESI+
Mobile phase: methanol

Figure 4:
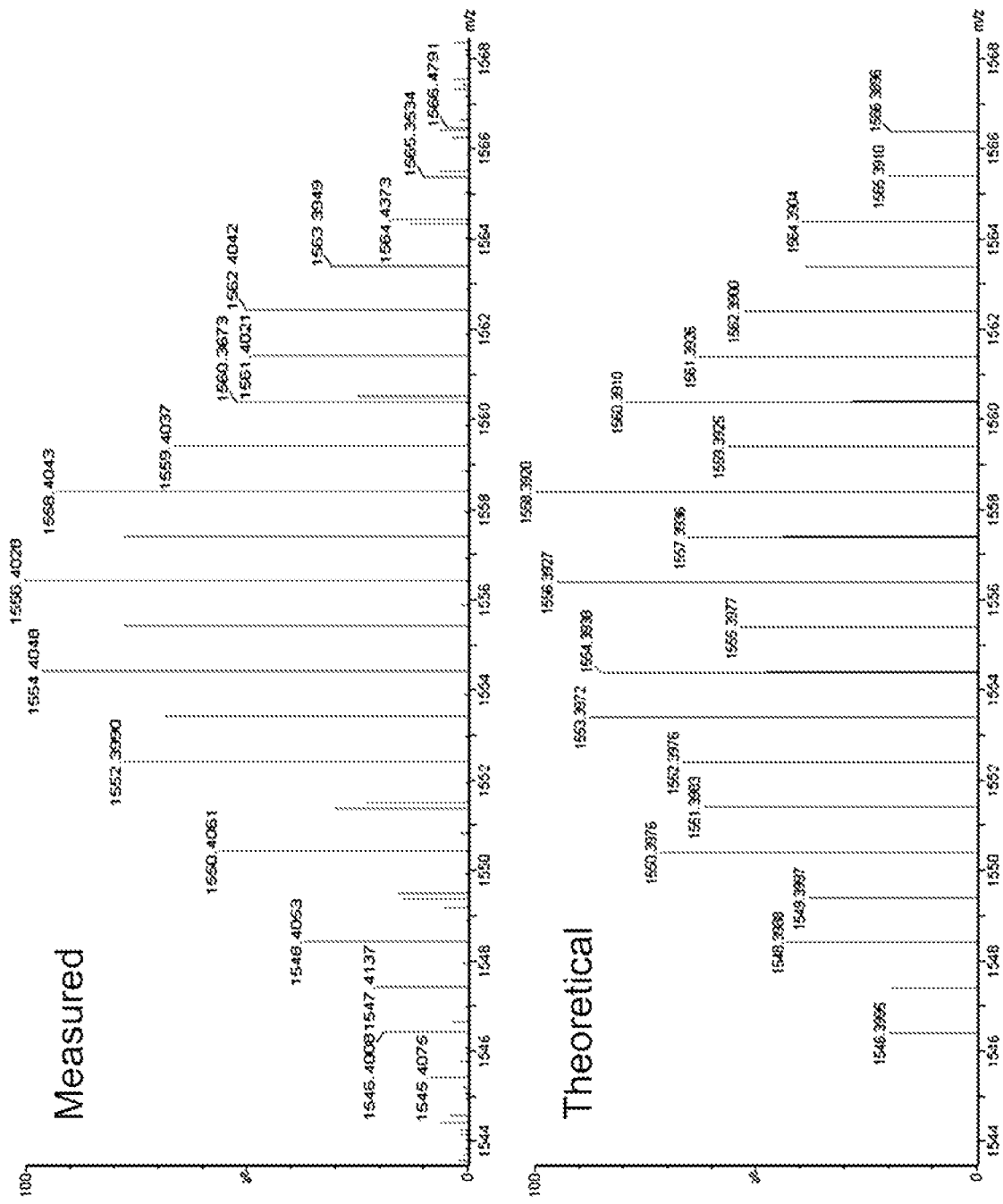
FIG. 4 is a diagram of the mass spectrum, measured by Time of Flight Mass Spectrometry (TOF-MS), of the THGP octamer and the theoretical spectrum of the THGP octamer.

FIG. 4 illustrates the mass spectrum of the THGP octamer measured by TOF-MS and the theoretical spectrum calculated from the amount of a natural isotope. It was confirmed that the measured values were largely consistent with the theoretical values.

8) $^1$H NMR Measurement

The $^1$H NMR spectrum of solutions of THGP octamer dissolved in heavy water and heavy methanol, respectively, were measured using a nuclear magnetic resonance spectrometer (Gemini 2000, Agilent Technologies, Inc.). For comparison, a solution of Ge-132 dissolved in heavy water and then neutralized with heavy sodium hydroxide solution was prepared and measured in the same way. The measurement conditions were 25° C., 16 scans, 300 MHz, and the signal of residual HOD was offset to 4.80 ppm.

Figure 5:
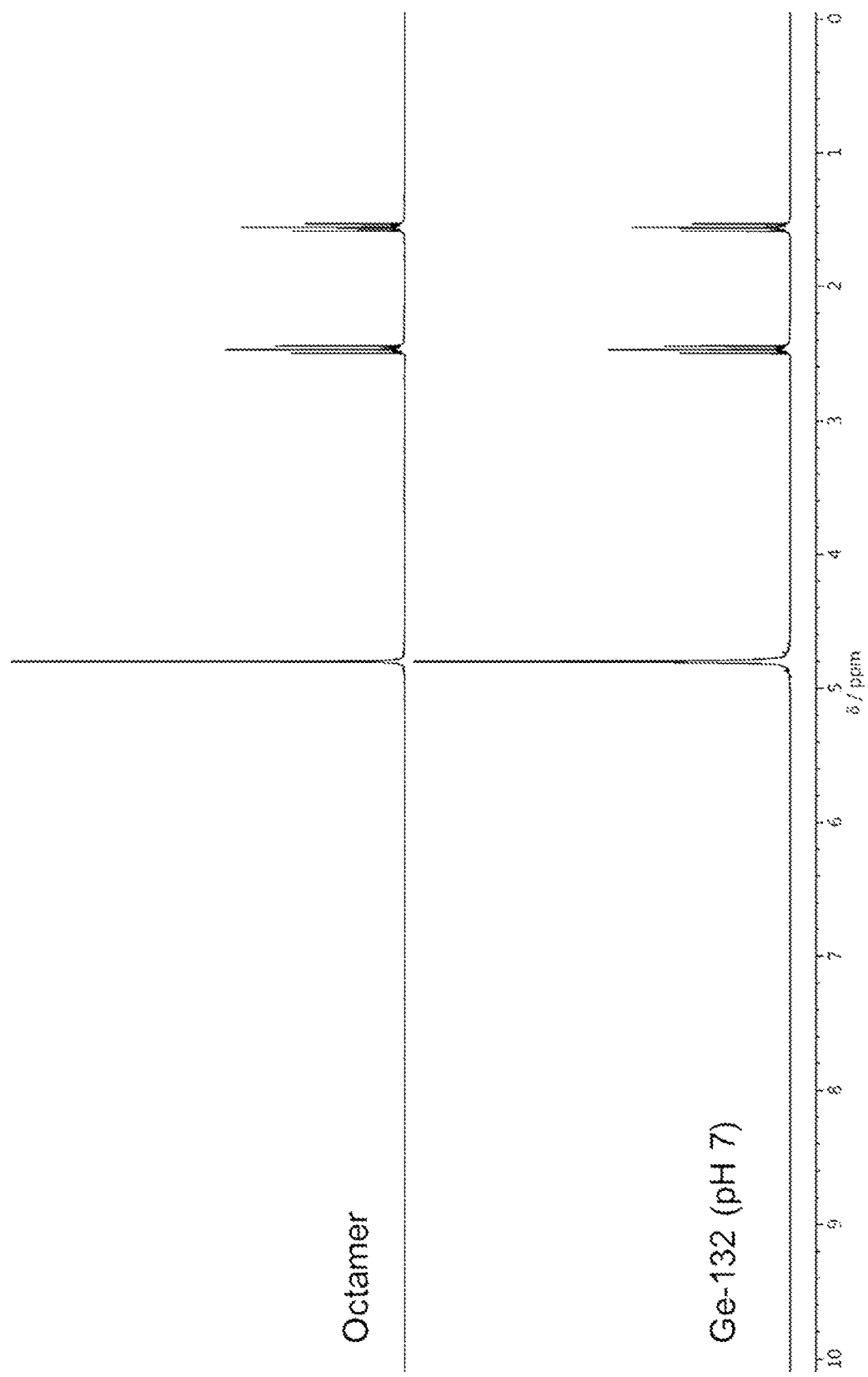
FIG. 5 is a diagram of the $^1$H NMR spectrum of the THGP octamer and the $^1$H NMR spectrum of Ge-132.
Figure 6:
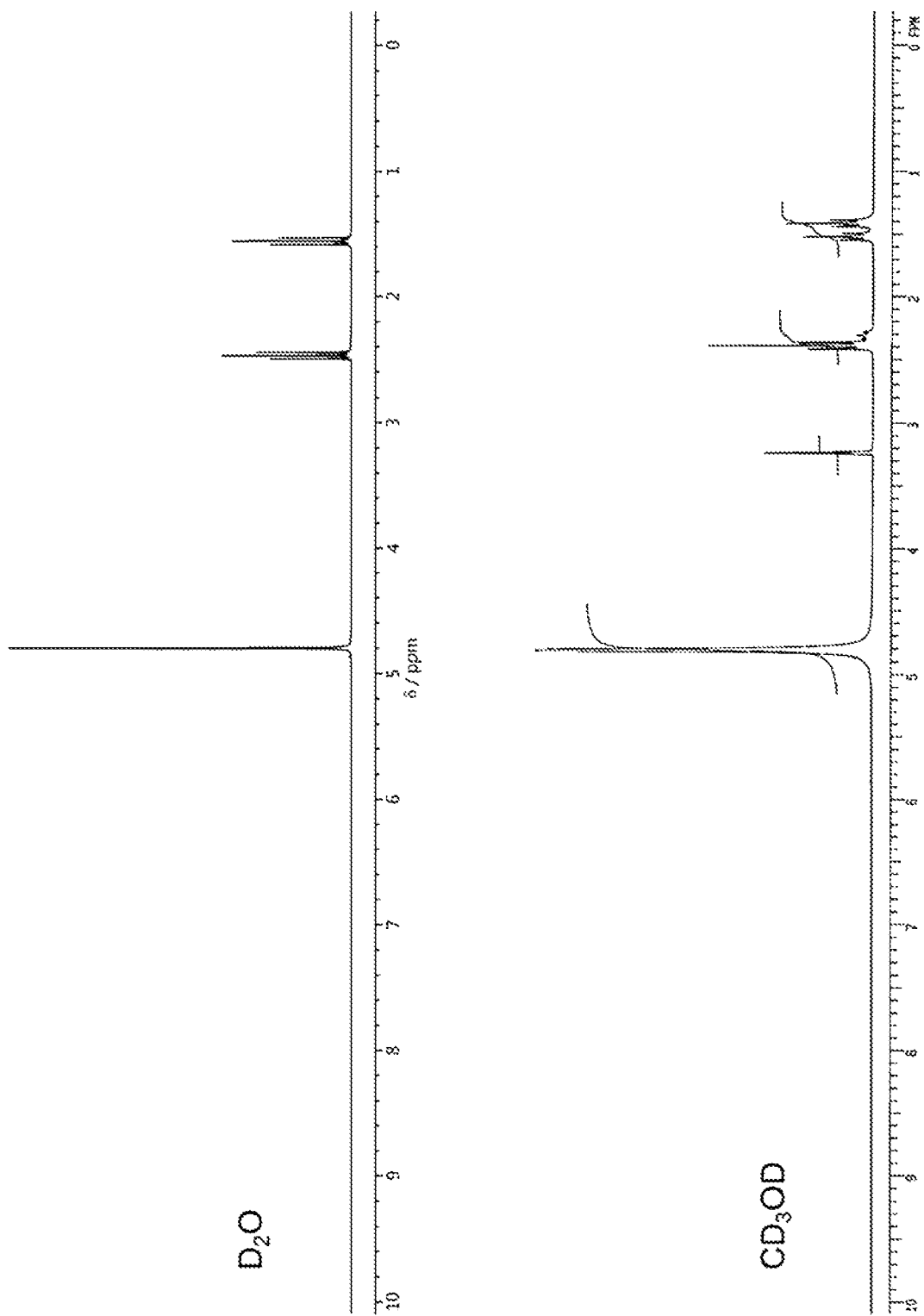
FIG. 6 is a diagram of the $^1$H NMR spectrum of the THGP octamer, obtained using heavy water and a heavy methanol solvent.

FIG. 5 and FIG. 6 illustrate the $^1$H NMR spectra of the samples. In the $^1$H NMR spectrum obtained by dissolving the THGP octamer in heavy water, triplet signals were observed at 1.56 ppm and 2.47 ppm, respectively. This result is consistent with those observed in the $^1$H NMR spectrum of the Ge-132 aqueous solution, suggesting that THGP was produced in both cases (see FIG. 5). In contrast, in the $^1$H NMR spectrum obtained by dissolving the THGP octamer in heavy methanol, triplet signals were observed at 1.40 ppm, 1.51 ppm, 2.30 ppm, and 2.38 ppm, respectively (FIG. 6). It was presumed that, in the case of using heavy water, the THGP octamer was hydrolyzed to produce THGP, and the signals caused by the two $CH_2$s on the propion chain were observed at two locations, while, in the case of using heavy methanol, the THGP octamer was not hydrolyzed, and the two $CH_2$s on the linear propion chain and the two $CH_2$s on the cyclic propion chain in the octamer were distinguished, and the signals were observed at four locations in total.

Example 2 Confirmation of Interactivity with Adenosine

The $^1$H NMR spectrum of a mixed solution obtained by dissolving the THGP octamer and adenosine (mixing molar ratio 1:1, pH 7.0 to 7.5, 100 mM) in heavy water was measured under the measurement conditions of 30° C., scan times of 16, and 300 MHz. The signal of residual HOD was offset to 4.80 ppm. For comparison, a mixed solution of Ge-132 and adenosine was measured in the same way.

Figure 7:
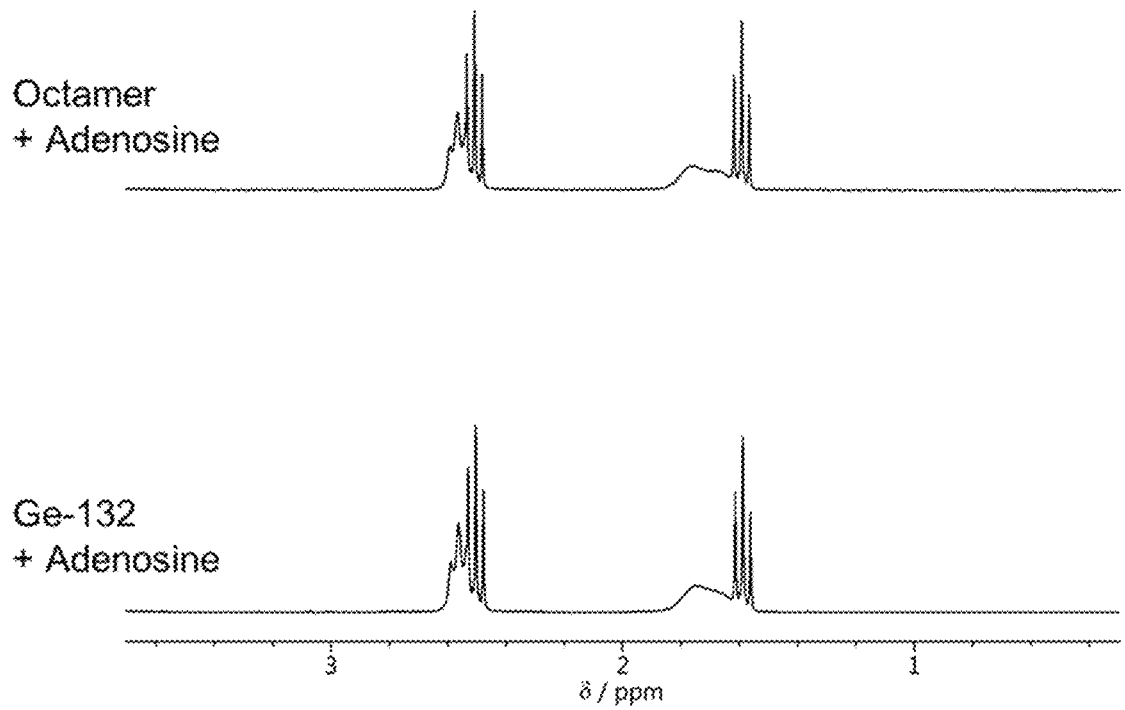
FIG. 7 is a diagram of the $^1$H NMR spectra of a mixed solution of adenosine and the THGP octamer or Ge-132.

FIG. 7 illustrates the $^1$H NMR spectra of the samples. In the $^1$H NMR spectrum of the mixed solution of the THGP octamer and adenosine, in addition to the triplet signals originated from THGP at 1.58 ppm (due to Ge—CH$_2$) and 2.50 ppm (due to CH$_2$—COO$^-$), new signals were observed at 1.76 ppm and 2.57 ppm. Since adenosine alone does not have a spectrum near the above chemical shifts, the newly observed signals were suggested to be originated from a complex of adenosine and THGP. This result is consistent with those observed in the $^1$H NMR spectrum obtained when Ge-132 was used in place of the THGP octamer, demonstrating that the THGP octamer generates THGP and shows reactivity with adenosine, as in the case of Ge-132.

Example 3 Confirmation of Interactivity with H$_2$S

The $^1$H NMR spectrum of a mixed solution obtained by dissolving the THGP octamer and NaHS (a sodium salt of H$_2$S) (mixing molar ratio 1:1, pH 7.0 to 7.5, 20 mM) in a 10 mM phosphate buffer (pH 7.4) prepared with heavy water, was measured under the measurement conditions of 25° C., scan times of 16, and 300 MHz. The signal of residual HOD was offset to 4.80 ppm. For comparison, a mixed solution of Ge-132 and NaHS was measured in the same manner.

Figure 8:
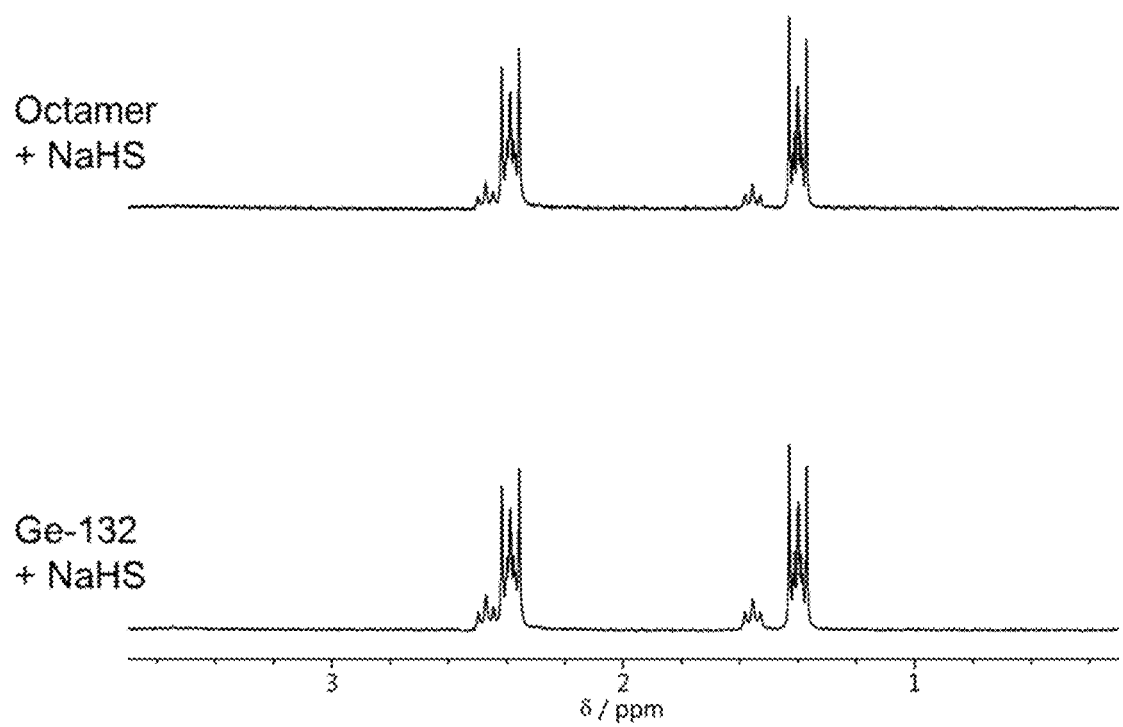
FIG. 8 is a diagram of the $^1$H NMR spectra of a mixed solution of NaHS (a sodium salt of $H_2S$) and the THGP octamer or Ge-132.

FIG. 8 illustrates the $^1$H NMR spectra of the samples. In the $^1$H NMR spectrum of the mixed solution of the THGP octamer and NaHS, in addition to the triplet signals originated from THGP at 1.56 ppm (due to Ge—CH$_2$) and 2.47 ppm (due to CH$_2$—COO$^-$), new signals were observed at 1.40 ppm and 2.39 ppm. Since NaHS alone does not have a spectrum near the above chemical shifts, the newly observed signals were suggested to be originated from a complex of THGP and NaHS. This result is consistent with those observed in the $^1$H NMR spectrum obtained when Ge-132 was used in place of the THGP octamer, demonstrating that the THGP octamer generates THGP and shows reactivity with NaHS, as in the case of Ge-132.

The invention claimed is:

1. A compound of formula (I),

[Chemical Formula 1]

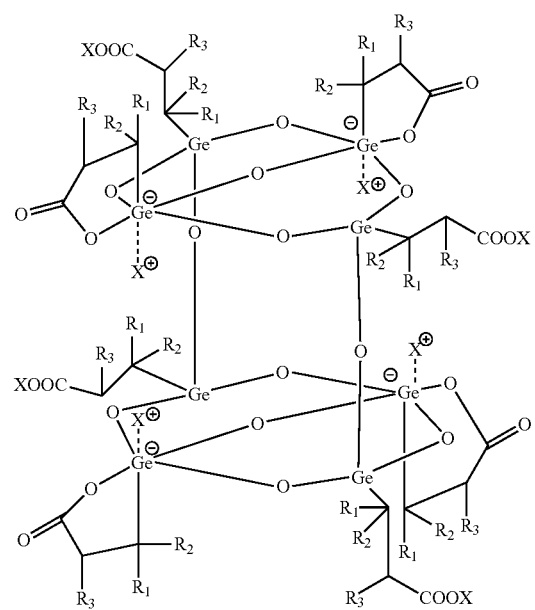

(I)

wherein R$_1$, R$_2$, and R$_3$ are each independently hydrogen or lower alkyl; and X is an alkali metal cation, an ammonium cation, or a quaternary ammonium cation.

2. The compound according to claim 1, wherein all of R$_1$, R$_2$, and R$_3$ are hydrogen.

3. The compound according to claim 1, wherein X is a sodium cation.

4. The compound according to claim 1, wherein all of R$_1$, R$_2$, and R$_3$ are hydrogen, and X is a sodium cation.

* * * * *

UNITED STATES PATENT AND TRADEMARK OFFICE
CERTIFICATE OF CORRECTION

PATENT NO. : 11,981,693 B2
APPLICATION NO. : 17/442450
DATED : May 14, 2024
INVENTOR(S) : Takashi Nakamura, Katsuyuki Sato and Yasuhiro Shimada Page 1 of 2

It is certified that error appears in the above-identified patent and that said Letters Patent is hereby corrected as shown below:

In the Claims

Column 14 Lines 5-30 In Claim 1, delete

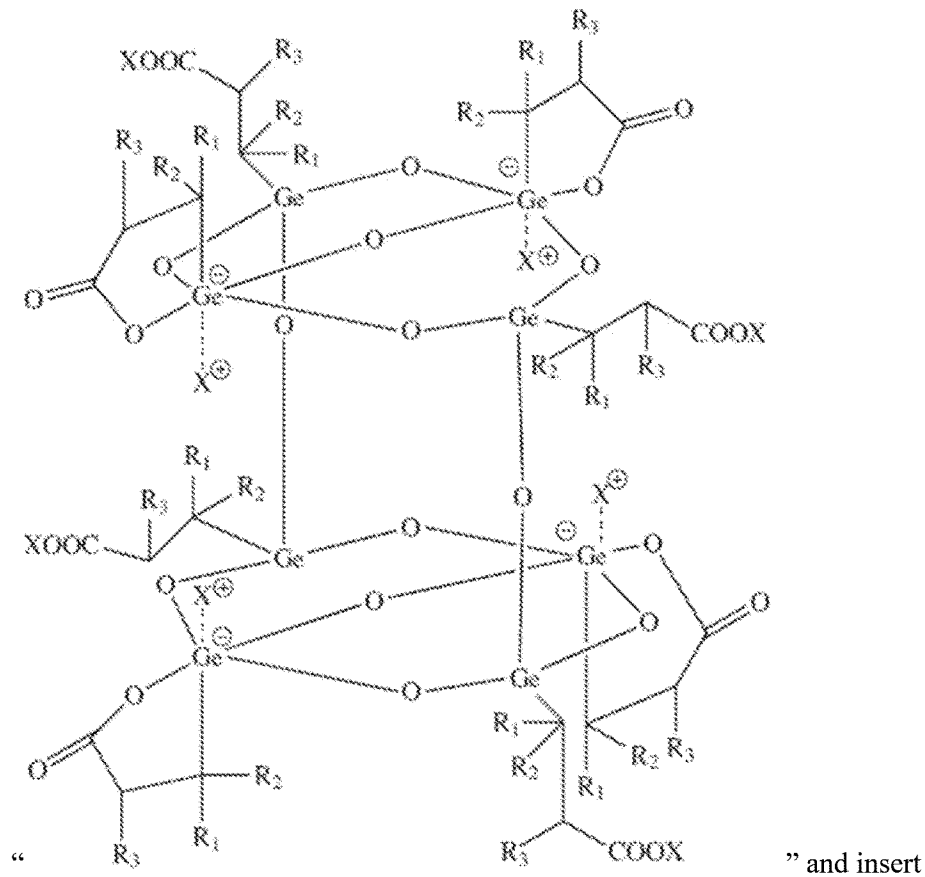

" and insert

Signed and Sealed this
Fifteenth Day of October, 2024

Katherine Kelly Vidal
*Director of the United States Patent and Trademark Office*

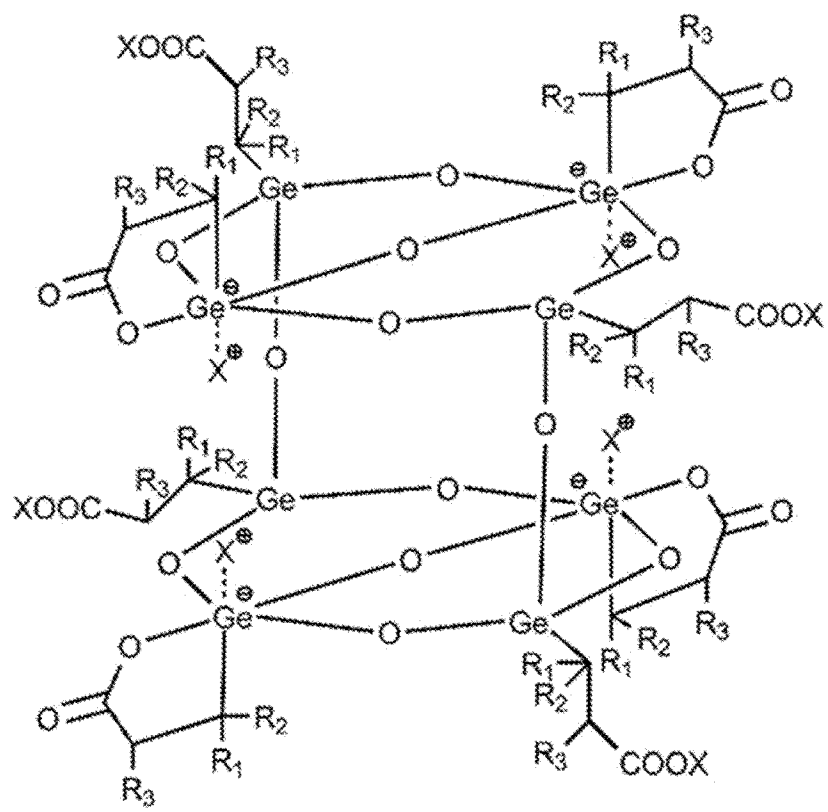
-- (I) --.